US010617076B2

(12) United States Patent
Shimada et al.

(10) Patent No.: US 10,617,076 B2
(45) Date of Patent: Apr. 14, 2020

(54) STALK-LENGTH-RELATED MARKER DERIVED FROM GENOME OF WILD-TYPE SUGARCANE AND USE THEREOF

(71) Applicant: TOYOTA JIDOSHA KABUSHIKI KAISHA, Toyota-shi, Aichi (JP)

(72) Inventors: Takehiko Shimada, Nagoya (JP); Hiroyuki Enoki, Hamamatsu (JP); Satoru Nishimura, Nagoya (JP); Tatsuro Kimura, Kariya (JP); Momoe Suitou, Toyohashi (JP); Shoko Ishikawa, Nishinoomote (JP); Takayoshi Terauchi, Nishinoomote (JP); Taiichiro Hattori, Nishinoomote (JP); Takeo Sakaigaichi, Koshi (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 0 days.

(21) Appl. No.: 14/388,161

(22) PCT Filed: Mar. 26, 2013

(86) PCT No.: PCT/JP2013/058698
§ 371 (c)(1),
(2) Date: Sep. 25, 2014

(87) PCT Pub. No.: WO2013/146738
PCT Pub. Date: Oct. 3, 2013

(65) Prior Publication Data
US 2015/0052631 A1    Feb. 19, 2015

(30) Foreign Application Priority Data
Mar. 26, 2012   (JP) .................. 2012-069850

(51) Int. Cl.
*A01H 1/04*   (2006.01)
*C12Q 1/68*   (2018.01)
*C12Q 1/6895*   (2018.01)

(52) U.S. Cl.
CPC ............ *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 8,519,223 B2 | 8/2013 | Taguchi et al. |
| 2009/0094717 A1 | 4/2009 | Troukhan et al. |
| 2009/0222941 A1 | 9/2009 | Taguchi et al. |
| 2011/0154528 A1 | 6/2011 | Ragot et al. |

FOREIGN PATENT DOCUMENTS

| JP | 2010-516236 A | 5/2010 |
| JP | 2012-50429 A | 3/2012 |
| WO | 2007/125958 A1 | 11/2007 |
| WO | 2012/017679 A1 | 2/2012 |

OTHER PUBLICATIONS

Hoarau et al. (Theor. Appl. Genet. (2001) 103: pp. 84-97).*
Cordeiro et al. (Plant Science, 160, (2001), pp. 1115-1123).*
GenBank blast search of SEQ ID No. 1 (included in Office Action).*
Mauricio, 2001, Mapping Quantitative Trait Loci in Plants: Uses and Caveats for Evolutionary Biology, Nature Reviews Genetics 2: 370-381.*
Slate, 2005, Quantitative trait locus mapping in natural populations: progress, caveats and future directions, Molecular Ecology 14: 363-379.*
Y. -B. Pan, et al., "Molecular Genotyping of Sugarcane Clones with Microsatellite DNA Markers", Maydica, 2003, pp. 319-329, vol. 48.
Nathalie Piperidis, et al., "Comparative genetics in sugarcane enables structured and validation of marker-trait associations", Molecular Breeding, 2008, 233-247, vol. 21.
EMBL Accession No. CA124917.1 Sep. 25, 2003, 2 pages total.
GenBank Accession No. CA122736.1 Sep. 23, 2003, 2 pages total.
GenBank Accession No. CA257347.1 Sep. 26, 2003., 2 pages total.
GenBank Accession No. CA137323.1 Sep. 24, 2003., 2 pages total.
Ming et al., Genome Research, 11.12 (2001):2075-2084.
Arruda, P., Accession No. CA124917, SCQSLR1061A11.g LR1 Saccharum hybrid cultivar SP80-3280 cDNA clone SCQSLR1061A11 5-, mRNA sequence, Database (online), retrieved from http://www.ncbi.nlm.nih.gov/nucest/CA124917 on Feb. 11, 2014.
Ray Ming, et al., "QTL Analysis in a Complex Autopolyploid Genetic Control of Sugar Content in Sugarcane", Genome Research, Dec. 1, 2001, pp. 2075-2084.
R. Ming, et al., "Molecular dissection of complex traits in autopolyploids: mapping QTLs affecting sugar yield and related traits in sugarcane", Theoretical and Applied Genetics, Aug. 1, 2002, pp. 332-345, vol. 105, No. 2-3.
"SCQSLR1061A11.g LR1 Saccharum hybrid cultivar SP80-3280 cDNA clone SCQSLR1061A11 5', mRNA sequence.", EM_EST:CA124917, Sep. 25, 2003, 1 page.
H. Enoki, et al., "The 117th Meeting of the Japanese Society of Breeding, held in 2010", Mar. 25, 2010, 7 pages.
Communication, dated Feb. 11, 2014, issued by the U. S. Patent and Trademark Office in U.S. Appl. No. 13/988,711.
Communication, dated Apr. 17, 2014, issued by the U. S. Patent and Trademark Office in U.S. Appl. No. 13/988,711.
Notice of Allowance, dated Jan. 20, 2017, issued by the United States Patent and Trademark Office in U.S. Appl. No. 14/330,661.
Official communication and Corrected Notice of Allowability, dated Feb. 9, 2017, issued by the United States Patent and Trademark Office in U.S. Appl. No. 14/330,661.

(Continued)

Primary Examiner — Bratislav Stankovic
(74) Attorney, Agent, or Firm — Sughrue Mion, PLLC

(57) ABSTRACT

The invention provides a marker related to quantitative traits of a Gramineae plant, and in particular, stalk length. Such Gramineae stalk-length-related marker comprises a continuous nucleic acid region selected from a region sandwiched between the nucleotide sequence shown in SEQ ID NO: 1 and the nucleotide sequence shown in SEQ ID NO: 2 of a chromosome of the Gramineae plant.

4 Claims, 4 Drawing Sheets
Specification includes a Sequence Listing.

(56) References Cited

OTHER PUBLICATIONS

Notice of Allowability, dated May 16, 2017, issued by the United States Patent and Trademark Office in U.S. Appl. No. 14/330,661.
Aitken, K. S., et al., "Genetic control of yield related stalk traits in sugarcane", Theor. Appl. Genet., 2008, vol. 117, pp. 1191-1203.
Hoarau, J.-Y., et al., "Genetic dissection of a modern sugarcane cultivar (Saccharum spp.) .II. Detection of QTLs for yield components", Theor. Appl. Genet., 2002, vol. 105, pp. 1027-1037.
Communication dated Jul. 22, 2016, issued by the U.S. Patent and Trademark Office in U.S. Appl. No. 14/330,661.

\* cited by examiner

SEQUENCE LISTING

```
<160> NUMBER OF SEQ ID NOS: 5

<210> SEQ ID NO 1
<211> LENGTH: 74
<212> TYPE: DNA
<213> ORGANISM: Saccharum spontaneum

<400> SEQUENCE: 1
cacctgatat caaaagataa agtcataagt cagttaactg cagatgatat ttcagaacca    60
aaacagcaac tgtt                                                      74

<210> SEQ ID NO 2
<211> LENGTH: 50
<212> TYPE: DNA
<213> ORGANISM: Saccharum spontaneum

<400> SEQUENCE: 2
gctgtcttcg atacagctta cacgctcatg actagactcg ccgggcgcgt               50

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
cacgatggat ccagtgca                                                  18

<210> SEQ ID NO 4
<211> LENGTH: 16
<212> TYPE: DNA
<213> ORGANISM: Artificial Sequence
<220> FEATURE:
<223> OTHER INFORMATION: Synthetic DNA

<400> SEQUENCE: 4
ctggatccat cgtgca                                                    16

<210> SEQ ID NO 5
<211> LENGTH: 16
<212> TYPE: DNA
<213> ORGANISM: Artificial Sequence
<220> FEATURE:
<223> OTHER INFORMATION: Synthetic DNA

<400> SEQUENCE: 5
gatggatcca gtgcag                                                    16
```

STALK-LENGTH-RELATED MARKER DERIVED FROM GENOME OF WILD-TYPE SUGARCANE AND USE THEREOF

CROSS REFERENCE TO RELATED APPLICATIONS

This application is a National Stage of International Application No. PCT/JP2013/058698, filed on Mar. 26, 2013, which claims priority from Japanese Patent Application No. 2012-069850, filed on Mar. 26, 2012, the contents of all of which are incorporated herein by reference in their entirety.

TECHNICAL FIELD

The present invention relates to a stalk-length-related marker that can be used to select a Gramineae plant with traits relating to stalk length characteristics of a wild-type sugarcane species, and the use thereof.

BACKGROUND ART

Sugarcane has been cultivated as a raw material for sugar, liquor, and the like for edible use. In addition, sugarcane has been used as, for example, a raw material for biofuel in a variety of industrial fields. Under such circumstances, there is a need to develop novel sugarcane varieties having desirable characteristics (e.g., sugar content, enhanced vegetative capacity, sprouting capacity, disease resistance, insect resistance, cold resistance, an increase in leaf-blade-length, an increase in leaf area, and increased stalk length). Also, Gramineae plants, including sugarcane, are generally used for starting materials for alcoholic beverages and biofuels.

Hybridization of Gramineae plants, including sugarcane, rice, and maize, has been actively carried out in an attempt to improve existing varieties; i.e., production of new varieties with traits of interest. In general, the following three methods may be used for identification of a plant variety/line: "characteristics comparison" for comparison of characteristics data, "comparison during cultivation" for comparison of plants cultivated under the same conditions, and "DNA assay" for DNA analysis. There are many problems in line identification with characteristics comparison or comparison during cultivation, including low precision due to differences in cultivation conditions and long-term field research that requires a number of steps.

In particular, sugarcane plants are much larger than other crops, and it is accordingly difficult to conduct line identification via field research. Further, production of a novel sugarcane variety necessitates production of tens of thousands of hybrids via crossing, followed by seedling selection and stepwise selection of excellent lines. Eventually, 2 or 3 types of novel varieties having desired characteristics can be obtained. In order to produce a novel sugarcane variety, as described above, it is necessary to cultivate and evaluate an enormous number of lines, to prepare a greenhouse or field, and to undertake highly time-consuming efforts.

Therefore, it has been required to develop a method for identifying a Gramineae plant, and in particular, a sugarcane line, having desired characteristics with the use of markers present in the genome. In particular, upon production of a novel sugarcane variety, if excellent markers could be used to examine a variety of characteristics, the above problems particular to sugarcane would be resolved, and the markers would be able to serve as very effective tools. Since sugarcane plants have a large number of chromosomes (approximately 100 to 130) due to high polyploidy, however, the development of marker technology has been slow. While the USDA reported genotyping concerning sugarcane plants with the use of SSR markers (Non-Patent Document 1), the precision of genotyping is low because of the small numbers of markers and polymorphisms in each marker. In addition, the above genotyping is available only for American/Australian varieties, and therefore, it cannot be used for identification of the major varieties cultivated in Japan, Taiwan, India, or other countries, or lines that serve as useful genetic resources.

In addition, Non-Patent Document 2 suggests the possibility that a sugarcane genetic map can be produced by increasing the number of markers, comparing individual markers in terms of a characteristic relationship, and verifying the results. Non-Patent Document 2, however, does not disclose a sufficient number of markers, and markers linked to desired characteristics have not been found.

An example of marker development is that of an *Aphanornyces cochlioides*-resistant related marker in sugar beet disclosed in Patent Document 1. Also, Patent Document 2 discloses a technique for selecting a maize variety with the utilization of a marker linked to a trait of interest.

There are wild-type sugarcane species (scientific name: *Saccharum spontaneum* L.). Examples of known wild-type sugarcane species include *Glagah* found in Indonesia, *Saccharum spontaneum* found in Japan, and *Kash* (*Kans Grass*) found in the Bengali-speaking regions. *Glagah, Saccharum spontaneum*, and *Kash* are general names of wild-type sugarcane species in relevant areas. In order to designate a specific variety or line, according to need, individual systemic names that include information such as names of areas in which samples were obtained or numbers indicating relevant nations are occasionally used. In general, a wild-type sugarcane species is characterized by exuberant growth and high environmental tolerance, it has a stalk that is thin but strong, it is rich in fiber, and it has excellent tolerance against diseases and pests, such as dwarf disease and yellow streak virus. While sugar content is generally low, and it is 1% to 3% or lower in the case of *Glagah*, sugar content of some wild-type sugarcane species harvested in Japan exceeds 10%. That is, the degree of variation is large.

By means of interspecies crossing or intergeneric crossing with wild-type sugarcane species, excellent properties of wild-type sugarcane species in terms of stalk extension or multiple branching are introduced into sugar-producing varieties or Gramineae plant varieties other than sugarcane. Many interspecies hybrids have been found to be excellent in low-temperature extension and final stalk length through experiments, and the genome of a wild-type sugarcane species is deduced to have a distinct gene that causes increased stalk length. Such properties are not observed in sugar-producing varieties. However, no markers related to various properties of wild-type sugarcane species are known. At present, accordingly, it is necessary to perform laborious and time-consuming procedures as described above, in order to select interspecies or intergeneric hybrids with such properties.

PRIOR ART DOCUMENTS

Patent Documents

Patent Document 1: WO 2007/125958
Patent Document 2: JP 2010-516236 A

Non-Patent Documents

Non-Patent Document 1: Maydica 48, 2003, 319-329, "Molecular genotyping of sugarcane clones with microsatellite DNA markers"
Non-Patent Document 2: Nathalie Piperidis et al., Molecular Breeding, 2008, Vol. 21, 233-247

SUMMARY OF THE INVENTION

Object to be Attained by the Invention

The present invention provides a stalk-length-related marker derived from the genome of a wild-type sugarcane species linked to traits relating to stalk length of the wild-type sugarcane species, and the use thereof.

Means for Attaining the Object

The present inventors had conducted concentrated studies in order to attain the above object. They prepared many sugarcane plant markers, including those of wild-type sugarcane species, and linkage analysis between quantitative traits and markers in hybrid progeny lines. As a result, they discovered markers derived from wild-type sugarcane species and related to quantitative traits relating to stalk length. This has led to the completion of the present invention.

The present invention encompasses the following.

(1) A Gramineae stalk-length-related marker, which comprises a continuous nucleic acid region existing in a region sandwiched between the nucleotide sequence shown in SEQ ID NO: 1 and the nucleotide sequence shown in SEQ ID NO: 2 of a chromosome of a Gramineae plant.

(2) The Gramineae stalk-length-related marker according to (1), wherein the nucleic acid region comprises the nucleotide sequence shown in SEQ ID NO: 1 or 2 or a part thereof.

(3) The Gramineae stalk-length-related marker according to (1), wherein one of parent plants of the Gramineae plant is a plant of a wild-type sugarcane species.

(4) A method for producing a Gramineae plant having increased stalk length comprising: a step of extracting a chromosome of the Gramineae plant and/or a parent thereof; and a step of determining the presence or absence of the Gramineae stalk-length-related marker according to any one of (1) to (3) in the chromosome obtained in the previous step.

(5) The method for producing a Gramineae plant according to (4), wherein the Gramineae plant is in the form of a seed or young seedling and the chromosome is extracted therefrom.

(6) The method for producing a Gramineae plant according to (4), which further comprises a step of producing the Gramineae plant by subjecting a wild-type sugarcane species to crossing as one of the parents.

This description includes part or all of the content as disclosed in the description and/or drawings of Japanese Patent Application No. 2012-069850, which is a priority document of the present application.

Effects of the Invention

According to the present invention, a novel Gramineae stalk-length-related marker that is linked to stalk length that is one of quantitative traits of a Gramineae plant such as sugarcane can be provided. With the use of the Gramineae stalk-length-related marker of the present invention, the stalk length of a line obtained by crossing of Gramineae plants, such as plants of sugarcane lines, can be tested. Thus, a Gramineae plant characterized by increased stalk length can be identified in a very cost-effective manner.

EMBODIMENTS FOR CARRYING OUT THE INVENTION

Figure 1:
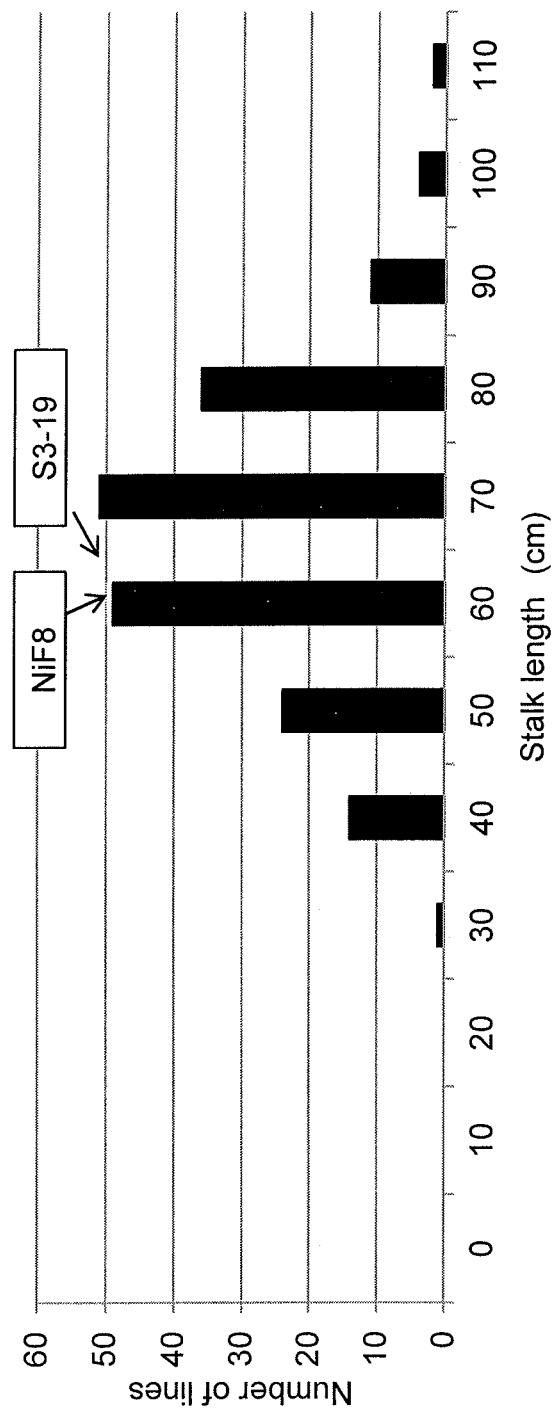
FIG. 1 is a characteristic diagram showing stalk-length data for sugarcane variety/line groups used in the Examples.

Hereafter, the Gramineae stalk-length-related marker and the method for using the same according to the present invention are described. In particular, a method for producing a Gramineae plant using the Gramineae stalk-length-related marker is described.

<Gramineae Stalk-length-related Marker>

The Gramineae stalk-length-related marker of the present invention corresponds to a specific region present on a chromosome of a Gramineae plant, such as sugarcane, and it is linked to causative genes (i.e., a group of genes) for traits that cause increased stalk length of a Gramineae plant, so that traits related to the stalk length of a Gramineae plant can be identified. Specifically, a progeny line obtained with the use of a Gramineae plant, such as a known sugarcane variety/line, can be determined to have traits that are characteristic of increased stalk length by confirming the presence or absence of the Gramineae plant stalk-length-related marker in such progeny line.

The Gramineae stalk-length-related marker of the present invention is linked to traits relating to increased stalk length. If a particular Gramineae plant comprises the Gramineae stalk-length-related marker of the present invention, for example, it can be determined that such plant has traits relating to increased stalk length. The term "increased stalk length" used herein refers to increased stalk length at the initial growth stage, in particular. In other words, such plant has a rapid stalk extension rate at the initial growth stage. The stalk length of sugarcane is the height from the plant base to the base of the first leaf (top visible dewlap leaf: +1) of the tallest stalk. In Japan, the initial stalk length is the stalk length during the first 5 months after germination, in general (and such duration can vary in accordance with the area of cultivation, cultivation conditions, and other factors).

The term "Gramineae plant" used herein refers to a plant that belongs to Gramineae, without particular limitation. That is, the Gramineae stalk-length-related marker of the present invention can be used for all plants classified as Gramineae plants. Plants. Gramineae plants are further classified as Bambusoideae, Pooideae, Ollyra, or Panicoideae.

Among Gramineae plants for which the Gramineae stalk-length-related marker of the present invention can be used, in particular, Bambusoideae includes plants of the genera *Arundinaria, Bambusa, Chimonobambusa, Chusquea, Dendrocalamus, Melocanna, Oxytenanthera, Phyllostachys, Pleioblastus, Pseudosasa, Sasa, Sasamorpha, Semiarundinaria, Shibataea, Sinobambusa*, and *Tetragonocalamus*.

Among Gramineae plants for which the Gramineae stalk-length-related marker of the present invention can be used, Pooideae includes plants of the genera *Beckmannia, Brachypodium, Briza, Bromus, Dactylis, Festuca, Glyceria, Lamarckia, Lolium, Melica, Poa, Puccinellia, Sesleria, Triodia, Agropyron, Elymus, Horudeum, Secale, Triticum, Agrostis, Arrhenatherum, Avena, Deschampsia, Helictotrichon, Holcus, Koeleria, Lagurus, Arundo, Cortaderia, Hakonechloa, Molinia, Phragmites, Arundinella, Loudetia, Tristachya, Phalaris, Spartina, Milium*, and *Stipa*.

Among Gramineae plants for which the Gramineae stalk-length-related marker of the present invention can be used, *Micraira* includes plants of the genus *Micraira*.

Among Gramineae plants for which the Gramineae stalk-length-related marker of the present invention can be used, *Eragrostis* includes plants of the genera *Diplachne, Eleusine, Eragrostis, Muhlenbergia, Sporobolus, Tripogon, Chloris, Cynodon, Aristida*, and *Zoysia*.

Among Gramineae plants for which the Gramineae stalk-length-related marker of the present invention can be used, the Gramineae subfamily includes plants of the genera *Leersia, Oryza*, and *Zizania*.

Among Gramineae plants for which the Gramineae stalk-length-related marker of the present invention can be used, the subfamily *Ollyra* includes plants of the genera *Ollyra, Cryptochloa*, and *Leptaspis*.

Among Gramineae plants for which the Gramineae stalk-length-related marker of the present invention can be used, the subfamily Panicoideae includes plants of the genera *Brachiaria, Digitaria, Echinochloa, Panicumn, Paspalum, Pennisetum, Setaria, Isachne, Andropogon, Schizoachyrium, Arthraxon, Bothriochloa, Cymbopogon, Dimeria, Eccoilopus, Erianthus, Eremochloa, Eulalia, Hemarthria, Imperata, Ischaemum, Microstegium, Miscanthus, Phacelurus, Pogonatherum, Saccharum, Sorghum, Themeda, Coix*, and *Zea*.

The Gramineae stalk-length-related marker of the present invention is applicable to all Gramineae plants classified as members of the subfamilies described above. Specifically, it is possible to determine that progeny lines of such Gramineae plants have traits characterized by increased stalk length by confirming the presence or absence of the Gramineae plant stalk-length-related marker of the present invention therein.

As a Gramineae plant to which the Gramineae stalk-length-related marker of the present invention is to be applied, a plant of *Schizachyrium* to which *Saccharum* belongs and a progeny line thereof are particularly preferable. With the use of the Gramineae stalk-length-related marker of the present invention, it is preferable to inspect traits related to stalk length of a progeny line obtained by crossing one sugarcane line with another line. Interspecies crossing or intergeneric crossing of a plant of *Saccharum* and a plant such as *Miscanthus, Sorghum*, or *Erianthus*, can be carried out in accordance with a conventional technique.

The term "sugarcane" used herein refers to a plant belonging to the genus *Saccharum* of the family Gramineae. In addition, the term "sugarcane" refers to any of the so-called noble canes (scientific name: *Saccharum officinarum*), wild canes (scientific name: *Saccharum spontaneum*), *Saccharum barberi, Saccharum sinense*, and *Saccharum robustum*, which is a progenitor cane of *Saccharum officinarum*. The term "known sugarcane variety/line" is not particularly limited. It includes any variety/line that can be used in Japan and any variety/line that is used outside Japan. Examples of sugarcane varieties cultivated in Japan include, but are not limited to, Ni1, NiN2, NiF3, NiF4, NiF5, Ni6, NiN7, NiF8, Ni9, NiTn10, Ni11, Ni12, Ni14, Ni15, Ni16, Ni17, NiTn19; NiTn20, Ni22, and Ni23. Examples of major sugarcane varieties in Japan include, but are not particularly limited to, NiF8, Ni9, NiTn10, and Ni15. In addition, examples of major sugarcane varieties that have been introduced into Japan include, but are not particularly limited to, F177, NCo310, and F172. Examples of wild-type sugarcane species include, but are not particularly limited to, *Glagah Kloet, Glagah* 1286, Mandalay, SES14, US56-15-8, and JW599.

In particular, it is preferable to determine traits related to stalk length of a progeny line obtained by crossing using a wild-type sugarcane species having excellent properties in terms of initial stalk length and/or a progeny line of such wild-type species (e.g., S3-19) as a parent line with the use of the Gramineae stalk-length-related marker of the present invention. The Gramineae stalk-length-related marker of the present invention corresponds to a chromosome region of the S3-19 line derived from *Glagah*, which is a wild-type sugarcane species excellent in terms of initial stalk length, and such marker is linked to traits relating to the stalk length of such wild-type species. Through detection of the presence or absence of the Gramineae stalk-length-related marker of the present invention, accordingly, whether or not the target progeny line has inherited traits of excellent initial stalk length can be determined.

In addition, a progeny line may be obtained by sibling cross in which a mother plant and a father plant are both a sugarcane variety/line, or it may be a hybrid line obtained from parent plants when one of which is a sugarcane variety/line and the other of which is a closely related variety/line (i.e., *Erianthus arundinaceus*). In addition, a progeny line may be obtained via so-called backcrossing.

The Gramineae stalk-length-related marker of the present invention has been newly identified by quantitative trait loci (QTL) analysis using a genetic linkage map containing 9,485 NiF8-derived markers and 11,238 S3-19-derived markers obtained from signal data of NiF8, S3-19, and hybrid line 214 and stalk length data. Many genes are presumably associated with stalk length, which is a quantitative trait exhibiting a continuous distribution. QTL analysis is carried out using QTL Cartographer gene analysis software (Wang S., C. J. Basten, and Z. B. Zeng, 2010; QTL Cartographer 1.17. Department of Statistics, North Carolina State University, Raleigh, N.C.) in accordance with the composite interval mapping (CIM) method. Also, the 9,485 NiF8-derived markers and the 11,238 S3-19-derived markers originally obtained from the sugarcane chromosomes may be selected with the use of DNA microarrays comprising probes designed in accordance with the methods disclosed in JP 2011-120558 A and WO 2011/074510.

Specifically, a region with an LOD score equivalent to or exceeding a given threshold (e.g., 2.5) was found in the above genetic linkage map using QTL analysis as described above. That is, a region of approximately 5.38 cM (centimorgans) was identified at a position of approximately 93.72 cM of the 10th linkage group of S3-19 as a QTL region associated with the stalk length. The term "morgan(s) (M)" used herein refers to a unit representing the relative distance between genes on a chromosome, and it is expressed as a percentage of the crossover rate. In the case of a sugarcane chromosome, 1 cM corresponds to approximately 2,000 kb. In addition, it is suggested that causative genes (i.e., a group of genes) for traits that cause increased stalk length in S3-19 or its parent strain (i.e., wild-type *Glagah*) could be present at the peak positions or in the vicinity thereof.

The 5.38-cM region is sandwiched between the marker S310951 and the marker S311375 shown in Table 1 below.

TABLE 1

| Linkage group | Marker name | Nucleotide sequence information | Signal threshold | SEQ ID NO: |
|---|---|---|---|---|
| 10 | S310951 | CACCTGATATCAAAAGATA AAGTCATAAGTCAGTTAAC TGCAGATGATATTTCAGAA CCAAAACAGCAACTGTT | 2353 | SEQ ID NO: 1 |
|  | S311375 | GCTGTCTTCGATACAGCTT ACACGCTCATGACTAGACT CGCCGGGCGCGT | 1176 | SEQ ID NO: 2 |

In Table 1, "Linkage group" represents the number given to each group among a plurality of linkage groups specified by QTL analysis, "Marker name" represents the name given to each marker originally obtained in the present invention, and "Signal threshold" represents the threshold used for determination of the presence or absence of a marker.

A nucleic acid region containing markers shown in Table 1 can be used as a Gramineae plant stalk-length-related marker. The term "nucleic acid region" used herein refers to a region comprising a nucleotide sequence having 95% or less, preferably 90% or less, more preferably 80% or less, and most preferably 70% or less identity to a different region that is present on a chromosome of the Gramineae plant. If the identity of a nucleic acid region serving as a Gramineae stalk-length-related marker to a different region is within the above range, the nucleic acid region can be specifically detected in accordance with a conventional technique. The identity level described herein can be calculated using default parameters and BLAST or a similar algorithm.

In addition, the nucleotide length of a nucleic acid region serving as a Gramineae stalk-length-related marker can be at least 8 nucleotides, preferably 15 nucleotides or more, more preferably 20 nucleotides or more, and the most preferably 30 nucleotides. If the nucleotide length of a nucleic acid region serving as a Gramineae stalk-length-related marker is within the above range, the nucleic acid region can be specifically detected in accordance with a conventional technique.

In particular, a Gramineae stalk-length-related marker is preferably selected from a 5.38-cM region; that is, a region sandwiched between the nucleotide sequence shown in SEQ ID NO: 1 and the nucleotide sequence shown in SEQ ID NO: 2. This is because the above peak is present in the region sandwiched between the nucleotide sequence shown in SEQ ID NO: 1 and the nucleotide sequence shown in SEQ ID NO: 2.

Further, a Gramineae stalk-length-related marker may be a nucleic acid region containing one of the two types of markers shown in Table 1. For example, it is preferable to use a nucleic acid region containing a marker (S310951) comprising the nucleotide sequence shown in SEQ ID NO: 1 or a nucleic acid region containing a marker (S311375) comprising the nucleotide sequence shown in SEQ ID NO: 2 as a Gramineae stalk-length-related marker. In such a case, the nucleotide sequence of a nucleic acid region containing the marker can be identified by a method for determining the nearest-neighbor sequence, such as inverse PCR, using primers designed based on the nucleotide sequence of such marker.

In addition, the two types of markers per se can be used as the Gramineae stalk-length-related markers. Specifically, at least one of the two types of markers can be used as a Gramineae stalk-length-related marker. For example, it is preferable to use a marker (S310951) consisting of the nucleotide sequence shown in SEQ ID NO: 1 or a marker (S311375) consisting of the nucleotide sequence shown in SEQ ID NO: 2 as a Gramineae stalk-length-related marker.

<Use of Gramineae Stalk-length-related Marker>

With the use of a Gramineae stalk-length-related marker, whether a Gramineae plant with a phenotype exhibiting an unknown stalk length has a phenotype of increased stalk length can be determined. The expression "the use of Gramineae stalk-length-related marker" used herein indicates the use of a DNA microarray having probes corresponding to the Gramineae stalk-length-related marker. The expression "probes corresponding to the Gramineae stalk-length-related marker" indicates oligonucleotides that can specifically hybridize under stringent conditions to the Gramineae stalk-length-related marker as defined above. For example, such oligonucleotides can be designed as partial or whole regions with nucleotide lengths of at least 10 continuous nucleotides, 15 continuous nucleotides, 20 continuous nucleotides, 25 continuous nucleotides, 30 continuous nucleotides, 35 continuous nucleotides, 40 continuous nucleotides, 45 continuous nucleotides, or 50 or more continuous nucleotides of the nucleotide sequence of the Gramineae stalk-length-related marker or a complementary strand thereof. In addition, a DNA microarray having such probes may be any type of microarray, such as a microarray having a planar substrate of glass or silicone as a carrier, a bead array comprising microbeads as carriers, or a three-dimensional microarray having an inner wall comprising hollow fibers to which probes are fixed.

With the use of a DNA microarray prepared as described above, whether a Gramineae plant line, such as a progeny line with a phenotype exhibiting an unknown stalk length has a phenotype of increased stalk length can be determined. Without the use of a DNA microarray, also, whether a Gramineae plant line with a phenotype exhibiting an unknown stalk length has a phenotype of increased stalk length can be determined by detecting the above Gramineae stalk-length-related marker in accordance with a conventional technique.

The method involving the use of a DNA microarray is described in greater detail in JP 2011-120558 A and WO 2011/074510. In accordance with such method, whether or not the target Gramineae plant comprises the Gramineae stalk-length-related marker of the present invention is detected. When the Gramineae stalk-length-related marker of the present invention is present, it can be determined that the target Gramineae plant line has traits that are characteristic of increased stalk length.

According to the method described above, in particular, it is not necessary to cultivate a target Gramineae plant, such as sugarcane, to such an extent that the actual stalk length thereof becomes measurable. For example, seeds of a progeny line or a young seedling obtained as a result of germination of such seeds can be used. With the use of the Gramineae stalk-length-related marker, accordingly, the area of a field used for cultivation of Gramineae plants and cost of cultivation can be reduced by a significant extent.

When producing a novel sugarcane variety, in particular, it is preferable to first produce several tens of thousands of hybrid varieties via crossing and then to identify a novel sugarcane variety using a Gramineae stalk-length-related marker prior to or instead of seedling selection. Thus, the number of excellent lines that need to be cultivated in an actual field can be reduced to a significant extent, and this can significantly reduce the labor and the cost required for production of a novel sugarcane variety.

Alternatively, the presence or absence of a Gramineae stalk-length-related marker in a parent line subjected to crossing may be first examined, so as to produce a novel sugarcane variety exhibiting increased stalk length. By producing a progeny line with the preferential use of a parent line exhibiting increased stalk length, a progeny line with a trait such as increased stalk length may be developed at high frequency. Thus, the number of satisfactory lines to be cultivated can be reduced to a significant extent, and the labor and the cost required for production of new Gramineae plants, such as sugarcane, can be reduced to significant extents.

EXAMPLES

Hereafter, the present invention is described in greater detail with reference to the following examples, although the technical scope of the present invention is not limited thereto.

<1. Production of DNA Microarray Probes>
(1) Materials

The following varieties were used: sugarcane varieties: NiF8, Ni9, US56-15-8, POJ2878, Q165, R570, Co290, and B3439; closely-related wild-type sugarcane varieties: *Glagah Kloet, Chunee, Natal Uba*, and *Robustum* 9; and *Erianthus* varieties: IJ76-349 and JW630.

(2) Restriction Enzyme Treatment

Genomic DNAs were extracted from the above sugarcane varieties, closely-related wild-type sugarcane varieties, and *Erianthus* varieties using DNeasy Plant Mini Kits (Qiagen). Genomic DNAs (750 ng each) were treated with a PstI restriction enzyme (25 units, NEB) at 37° C. for 2 hours. Thereafter, a BstNI restriction enzyme (25 units, NEB) was added thereto, and the resultant was subjected to treatment at 60° C. for 2 hours.

(3) Adapter Ligation

PstI sequence adapters (5'-CACGATGGATCCAGTGCA-3' (SEQ ID NO: 3) and 5'-CTGGATCCATCGTGCA-3' (SEQ ID NO: 4)) and T4 DNA Ligase (800 units, NEB) were added to the genomic DNA fragments treated in (2) (120 ng each), and the resultants were subjected to treatment at 16° C. for a full day. Thus, the adapters were selectively added to genomic DNA fragments having PstI recognition sequences at both ends thereof among the genomic DNA fragments treated in (2).

(4) PCR Amplification

A PstI sequence adapter recognition primer (5'-GATGGATCCAGTGCAG-3' (SEQ ID NO: 5)) and Taq polymerase (1.25 units, PrimeSTAR, TAKARA) were added to the genomic DNA fragment (15 ng) having the adaptors obtained in (3). The genomic DNA fragment was then amplified by PCR (30 cycles of 98° C. for 10 seconds, 55° C. for 15 seconds, and 72° C. for 1 minute, and treatment at 72° C. for 3 minutes, followed by storage at 4° C.).

(5) Genome Sequence Acquisition

The nucleotide sequence of the genomic DNA fragment amplified by PCR in (4) was determined using FLX454 (Roche) or by the Sanger method. In addition, information on a nucleotide sequence sandwiched between PstI recognition sequences was obtained based on the total sorghum genome sequence information stored in the genome database (Gramene: http://www.gramene.org/).

(6) Probe Design and DNA Microarray Production

On the basis of the genome sequence information in (5), 50- to 75-bp probes were designed. On the basis of the nucleotide sequence information of the designed probes, a DNA microarray having the probes was produced.

<2. Acquisition of Signal Data Using DNA Microarray>
(1) Materials

Sugarcane varieties/lines (NiF8 and 53-19) and the progeny line (line 214) were used.

(2) Restriction Enzyme Treatment

Genomic DNAs were extracted from NiF8, S3-19, and the progeny line (line 214) using DNeasy Plant Mini Kits (Qiagen). Genomic DNAs (750 ng each) were treated with a PstI restriction enzyme (25 units, NEB) at 37° C. for 2 hours. Thereafter, a BstNI restriction enzyme (25 units, NEB) was added thereto, and the resultant was subjected to treatment at 60° C. for 2 hours.

(3) Adapter Ligation

PstI sequence adapters (5'-CACGATGGATCCAGTGCA-3' (SEQ ID NO: 3) and 5'-CTGGATCCATCGTGCA-3' (SEQ ID NO: 4)) and T4 DNA Ligase (800 units, NEB) were added to the genomic DNA fragments treated in (2) (120 ng each), and the resultants were treated at 16° C. for a full day. Thus, the adaptors were selectively added to a genomic DNA fragment having PstI recognition sequences at both ends thereof among the genomic DNA fragments treated in (2).

(4) PCR Amplification

A PstI sequence adapter recognition primer (5'-GATGGATCCAGTGCAG-3' (SEQ ID NO: 5)) and Taq polymerase (1.25 units, PrimeSTAR, TAKARA) were added to the genomic DNA fragment (15 ng) having the adapters obtained in (3). The genomic DNA fragment was then amplified by PCR (30 cycles of 98° C. for 10 seconds, 55° C. for 15 seconds, and 72° C. for 3 minutes, and treatment at 72° C. for 3 minutes, followed by storage at 4° C.).

(5) Labeling

The PCR-amplified fragment obtained in (4) above was purified with a column (Qiagen), and Cy3-labeled 9mers (1 O.D., TriLink) was added thereto. The resultant was treated at 98° C. for 10 minutes and allowed to stand on ice for 10 minutes. Thereafter, Klenow (100 units, NEB) was added thereto, and the resultant was subjected to treatment at 37° C. for 2 hours. A labeled sample was then prepared by ethanol precipitation.

(6) Hybridization/Signal Detection

The labeled sample obtained in (5) was subjected to hybridization using the DNA microarray prepared in 1.

above in accordance with the NimbleGen Array User's Guide, and signals resulting from labeling were detected.

<3. Identification of Gramineae Stalk-length-related QTL and Development of Markers>

(1) Production of Genetic Map Datasheet

Genotype data of 9,485 possible NiF8-derived markers and 11,238 S3-19-derived markers were obtained based on the signal data of the NiF8 and S3-19 sugarcane varieties and the progeny line thereof (line 214) detected in 2. above. On the basis of the obtained genotype data, information on the marker position in the chromosome was obtained by calculation using the gene distance function (Kosambi) and AntMap genetic map production software (Iwata, H. and Ninomiya, S., 2006, AntMap: constructing genetic linkage maps using an ant colony optimization algorithm, Breed Sci. 56: 371-378). Further, a genetic map datasheet was produced on the basis of the obtained marker position information using Mapmaker/EXP ver. 3.0 (A Whitehead Institute for Biomedical Research Technical Report, Third Edition, January, 1993).

(2) Acquisition of Stalk Length Data

On Apr. 13, 2011, sugarcane varieties (NiF8 and S3-19) and the progeny line (line 214) were planted in 2 replicates at a planting density of 13 plants/2.2 $m^2$ per replicate. On Jul. 28, 2011, 5 individuals in each replicate were subjected to measurement of the height from the plant base to the base of the top visible dewlap leaf. The average obtained from the results for two replicates was employed as the sugarcane stalk-length data (cm). The stalk lengths of the measured sugarcane lines are collectively shown in FIG. 1. NiF8 and S3-19 were observed in the 62 (cm) and 67.7 (cm) data ranges, respectively.

(3) Quantitative Trait (Quantitative Trait Loci: QTL) Analysis

Figure 2:
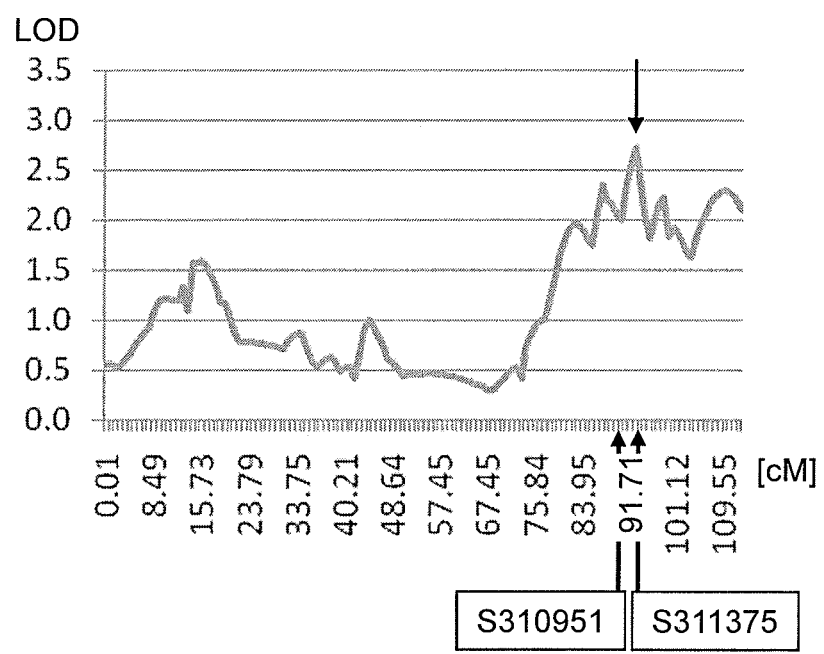
FIG. 2 is a characteristic diagram showing the results of QTL analysis regarding stalk length (the 10th linkage group of S3-19).

On the basis of the genetic map datasheet obtained in (1) above and the stalk length data obtained in (2) above, QTL analysis was carried out by the composite interval mapping (CIM) method using QTL Cartographer gene analysis software (Wang S., C. J. Basten, and Z.-B. Zeng, 2010, QTL Cartographer 1.17, Department of Statistics, North Carolina State University, Raleigh, N.C.). Upon analysis, the LOD threshold was determined to be 2.5. As a result, as shown in FIG. 2, a peak exceeding the LOD threshold was observed in a range between the markers S310951 and S311375 present in the 10th linkage group of the sugarcane line S3-19. As shown in Table 2, the obtained peak can be identified. This indicates the presence of causative genes (i.e., a group of genes) each having the function of causing increased stalk length at relevant peak positions. The column showing the effects (cm) in Table 2 quantitatively demonstrates the effects of causing increased stalk length.

TABLE 2

| Linkage group | Position (cM) | Range (cM) | Nearest marker | LOD value | Effects (cm) |
| --- | --- | --- | --- | --- | --- |
| S3-19 | 93.72 | 5.38 | S310951-S311375 | 2.73 | 6.1 |

Figure 4:
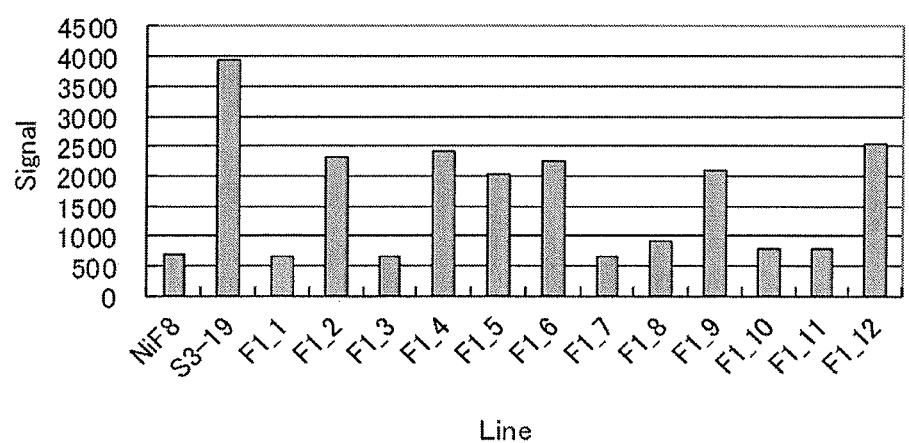
FIG. 4 is a characteristic diagram showing S311375 signal levels for individual lines.

As shown in FIG. 4, markers located in the vicinity of the relevant peaks are inherited in linkage with causative genes (i.e., a group of genes) each having the function of causing increased stalk length. This indicates that the markers can be used as Gramineae stalk-length-related markers. Specifically, the 2 types of markers shown in FIG. 4 were found to be usable as Gramineae stalk-length-related markers.

Figure 3:
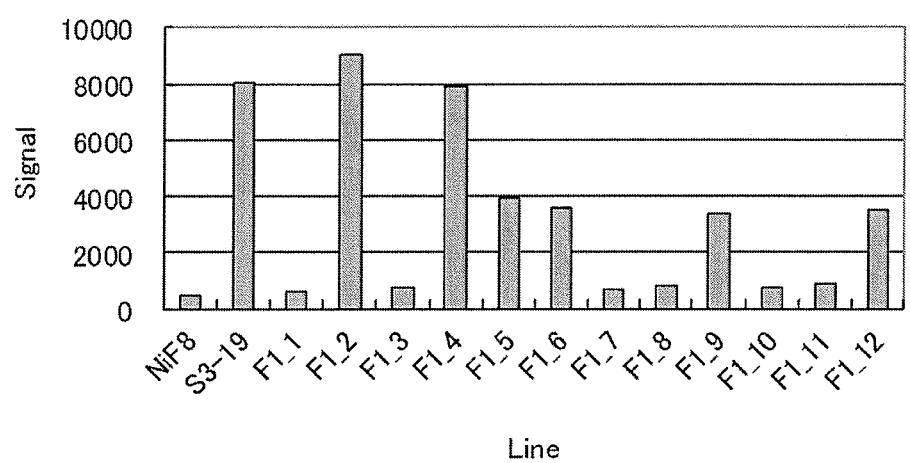
FIG. 3 is a characteristic diagram showing S310951 signal levels for individual lines.

As examples of signals detected in 2 (6) above, signal levels of markers S310951 and S311375 of NiF8, S3-19, and their 12 progeny lines are shown in Table 3 and FIGS. 3 and 4.

TABLE 3

| Linkage group | Marker name | NiF8 | S3-19 | F1_1 | F1_2 | F1_3 | F1_4 | F1_5 | F1_6 | F1_7 | F1_8 | F1_9 | F1_10 | F1_11 | F1_11 |
| --- | --- | --- | --- | --- | --- | --- | --- | --- | --- | --- | --- | --- | --- | --- | --- |
| S3-19 | S310951 | 433.1 | 8070.8 | 589.4 | 9039.3 | 731.6 | 7891.0 | 3973.0 | 3593.1 | 680.8 | 804.0 | 3389.8 | 737.8 | 885.3 | 3524.0 |
| C10 | S311375 | 699.7 | 3953.9 | 648.1 | 2329.8 | 640.5 | 2423.7 | 2017.0 | 2256.7 | 651.7 | 902.0 | 2101.2 | 789.1 | 778.7 | 2524.9 |

(4) Determination of Origins of Markers S310951 and S311375

Subsequently, the origins of markers S310951 and S311375 contained in the Gramineae stalk-length-related marker identified in (3) above were determined. Specifically, genomic homology between IRK67-1 and *Glagah*, which are parent lines of the sugarcane variety S3-19, was inspected via a DNA-array-based experiment. The experiment was carried out using a DNA array comprising probes designed in accordance with the method disclosed in JP 2011-120558 A. As a result, it was determined that the markers S310951 and S311375 identified in (3) were derived from *Glaga*, which is a wild-type sugarcane species, as shown in Table 4.

TABLE 4

| Marker, ID | S3-19, Chr | Position (cM) | Genotype | Glaga | IRK67-1 | Glaga_1 | Glaga_2 | IRK67-1_1 | IRK67-1_2 | Threshold |
| --- | --- | --- | --- | --- | --- | --- | --- | --- | --- | --- |
| S310951 | 10 | 88.33 | S3-19 | A | B | 13.4 | 13.4 | 9.0 | 8.9 | 11.2 |
| S311375 | 10 | 93.71 | S3-19 | A | B | 12.9 | 12.9 | 10.0 | 9.8 | 10.2 |

In Table 4, the results attained with the use of the same samples (i.e., Glaga_1 and Glaga_2) were obtained using the same samples in the DNA array. Also, the results attained with the use of IRK67-1_1 and IRK67-1_2 were obtained using the same sample. In Table 4, also, "A" indicates that the marker is derived from the genome of the variety indicated in the relevant column, and "B" indicates that the marker is not derived from the genome of the variety indicated in the relevant column.

All publications, patents, and patent applications cited herein are incorporated herein by reference in their entirety.

---

---

The invention claimed is:

1. A method for selecting a sugarcane progeny having increased stalk length, said method comprising:
producing sugarcane progeny by crossing, wherein at least one of the parent plants used for said crossing is a sugarcane plant, wherein said crossing is a sibling cross, a backcross, or a cross to produce a hybrid line;
extracting genomic DNA from at least one of said progeny plants;
analyzing said genomic DNA to detect the presence of a stalk-length-related marker in the extracted genomic DNA, and selecting a progeny plant with the marker in its genome, thereby selecting a sugarcane progeny having increased stalk length,
wherein said stalk-length-related marker comprises at least thirty consecutive nucleotides of the nucleotide sequence of SEQ ID NO:1, and at least thirty consecutive nucleotides of the nucleotide sequence of SEQ ID NO:2.

2. The method according to claim 1, wherein said progeny plant is in the form of a seed or young seedling and the genomic DNA is extracted therefrom.

3. The method according to claim 1, wherein said crossing uses at least one wild-type sugarcane species as a parent plant.

4. A method for selecting a sugarcane plant having increased stalk length, said method comprising:
- extracting genomic DNA from at least one sugarcane plant and/or a parent thereof;
- analyzing said genomic DNA to detect the presence of a stalk-length-related marker in the extracted genomic DNA, and selecting a sugarcane plant with the marker in its genome, thereby selecting a sugarcane plant having increased stalk length; and
- using the selected plant as a parent plant for crossing, to thereby produce progeny plant(s) containing said marker, wherein said crossing is a sibling cross, a backcross, or a cross to produce a hybrid line;
- wherein said Gramineae stalk-length-related marker comprises at least thirty consecutive nucleotides of the nucleotide sequence of SEQ ID NO:1, and at least thirty consecutive nucleotides of the nucleotide sequence of SEQ ID NO:2.

\* \* \* \* \*